(12) United States Patent
Kay et al.

(10) Patent No.: US 8,784,430 B2
(45) Date of Patent: Jul. 22, 2014

(54) NAIL CAP CANNULA

(75) Inventors: Michael Kay, Peru, IN (US); Rebecca Parrott, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 694 days.

(21) Appl. No.: 11/740,603

(22) Filed: Apr. 26, 2007

(65) Prior Publication Data

US 2008/0269744 A1 Oct. 30, 2008

(51) Int. Cl.
*A61B 17/90* (2006.01)

(52) U.S. Cl.
USPC .................. 606/104; 606/62; 606/96; 606/98

(58) Field of Classification Search
USPC ........................ 606/62–68, 104, 96
See application file for complete search history.

(56) References Cited

U.S. PATENT DOCUMENTS

| | | | | |
|---|---|---|---|---|
| 4,913,137 A | * | 4/1990 | Azer et al. ................. | 606/64 |
| 5,176,681 A | | 1/1993 | Lawes et al. | |
| 5,178,621 A | * | 1/1993 | Cook et al. ................. | 606/96 |
| 5,281,224 A | * | 1/1994 | Faccioli et al. ............ | 606/62 |
| 5,295,991 A | * | 3/1994 | Frigg ......................... | 606/62 |
| 5,403,321 A | * | 4/1995 | DiMarco .................... | 606/96 |
| 5,458,600 A | * | 10/1995 | Stapert et al. .............. | 606/63 |
| 5,478,341 A | * | 12/1995 | Cook et al. ................. | 606/62 |
| 5,489,284 A | * | 2/1996 | James et al. ................ | 606/62 |
| 5,549,610 A | * | 8/1996 | Russell et al. ............. | 606/64 |
| 5,626,580 A | * | 5/1997 | Brosnahan ................. | 606/63 |
| 5,665,086 A | * | 9/1997 | Itoman et al. .............. | 606/64 |
| 5,766,174 A | * | 6/1998 | Perry ......................... | 606/62 |
| 5,766,179 A | * | 6/1998 | Faccioli et al. ............ | 606/98 |
| 5,855,579 A | * | 1/1999 | James et al. ................ | 606/62 |
| 6,039,739 A | * | 3/2000 | Simon ........................ | 606/64 |
| 6,168,595 B1 | * | 1/2001 | Durham et al. ............ | 606/64 |
| 6,183,477 B1 | | 2/2001 | Pepper | |
| 6,514,253 B1 | * | 2/2003 | Yao ............................ | 606/53 |
| 7,901,410 B2 | * | 3/2011 | Bigdeli-Issazadeh et al. .. | 606/98 |
| 2003/0004513 A1 | * | 1/2003 | Guzman et al. ............ | 606/62 |
| 2003/0135211 A1 | * | 7/2003 | Cho ............................ | 606/62 |
| 2003/0149486 A1 | * | 8/2003 | Huebner ................. | 623/19.11 |
| 2004/0010252 A1 | * | 1/2004 | Zander et al. .............. | 606/53 |
| 2004/0082955 A1 | * | 4/2004 | Zirkle, Jr. ................... | 606/62 |
| 2004/0082959 A1 | * | 4/2004 | Hayes et al. ............... | 606/96 |
| 2005/0203520 A1 | | 9/2005 | Volzow | |
| 2006/0030864 A1 | * | 2/2006 | Kennedy, et al. .......... | 606/108 |
| 2009/0030418 A1 | * | 1/2009 | Volzow ...................... | 606/96 |
| 2009/0112209 A1 | * | 4/2009 | Parrott et al. .............. | 606/62 |

FOREIGN PATENT DOCUMENTS

| | | |
|---|---|---|
| EP | 0321170 B1 | 11/1994 |
| EP | 0486483 B1 | 2/1996 |
| EP | 0521600 B1 | 6/1996 |

* cited by examiner

*Primary Examiner* — Jerry Cumberledge
(74) *Attorney, Agent, or Firm* — Schwegman Lundberg & Woessner, P.A.

(57) ABSTRACT

A nail cap cannula for directing a nail cap useable with an intramedullary nail system including an intramedullary nail and a targeting guide.

18 Claims, 4 Drawing Sheets

FIG_1

FIG_2

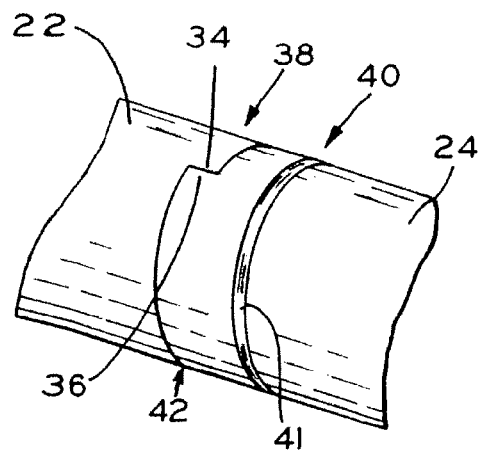
FIG.3
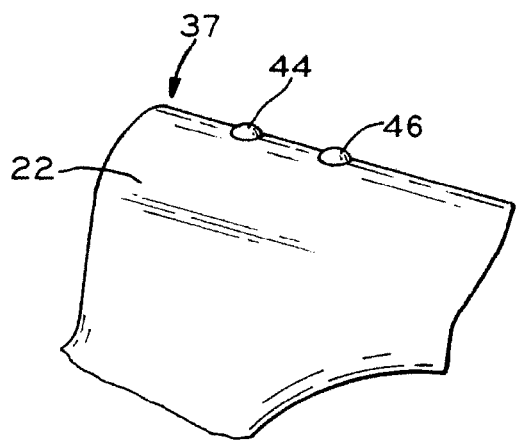
FIG.4
FIG.8
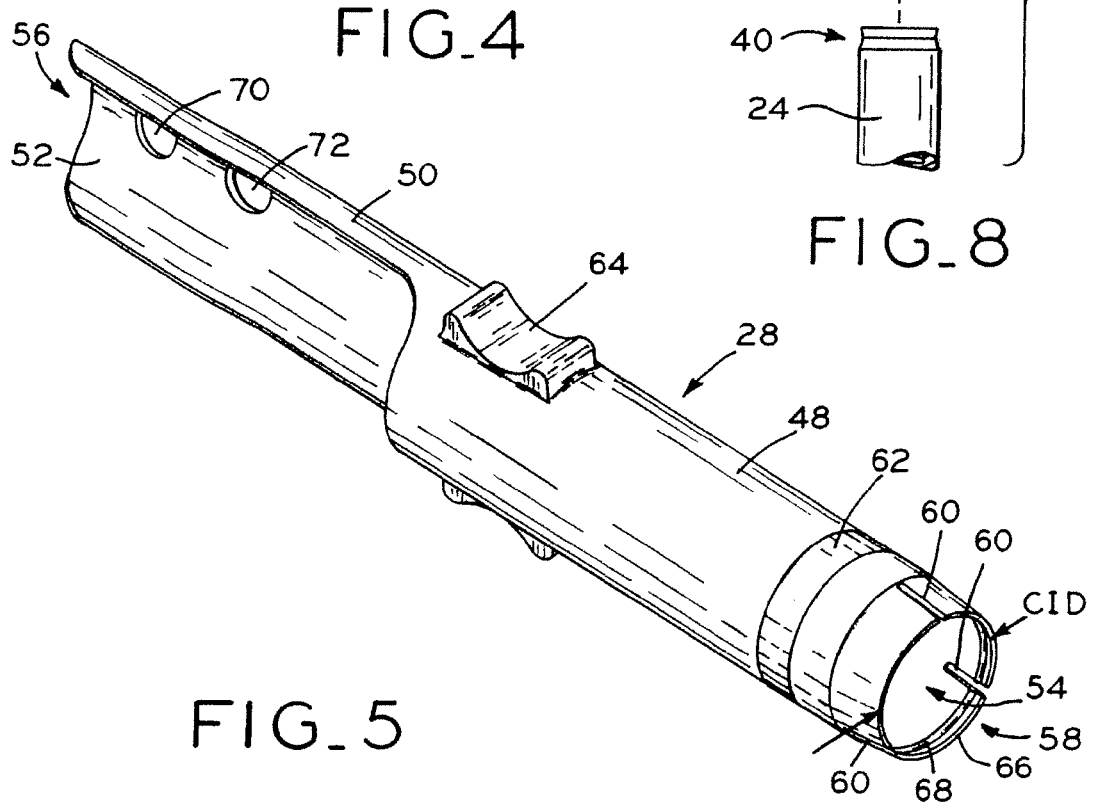
FIG.5

NAIL CAP CANNULA

BACKGROUND AND SUMMARY

The present disclosure relates to an intramedullary nail system. More particularly, the present disclosure relates to a nail cap cannula useable with an intramedullary nail system.

Intramedullary nail systems typically include an intramedullary nail and a targeting guide used to accurately position the nail in an intramedullary canal of an anatomical structure, such as a femur, for example.

In one form, the present disclosure provides a nail cap cannula for directing a nail cap useable with an intramedullary nail system.

In one form thereof, the present disclosure provides a nail cap cannula for use with an intramedullary nail system, the intramedullary nail system including a targeting guide, a nail cap cannula, and an intramedullary nail with an external mating surface adjacent to a first end of the nail, the nail cap cannula including a substantially hollow body portion including a first end and a second end, the first end including an internal mating surface configured to mate with the external mating surface of the intramedullary nail; the cannula movable between a disengaged position relative to the intramedullary nail, in which the internal mating surface of the cannula is disengaged from the external mating surface of the intramedullary nail, and an engaged position relative to the intramedullary nail, in which the internal mating surface of the cannula is engaged with the external mating surface of the intramedullary nail.

In another form thereof, the present disclosure provides a nail cap cannula for use with an intramedullary nail system including a nail cap cannula, a targeting guide, a nail cap, and an intramedullary nail, the cannula including a substantially hollow body portion having a passageway for permitting passage of the nail cap through the cannula; and retaining means for retaining the intramedullary nail with the cannula after removal of the targeting guide.

In yet another form thereof, the present disclosure provides a method of performing a surgical procedure on an anatomical structure using an intramedullary nail system including a targeting guide, a nail cap, and an intramedullary nail, the method including the steps of providing an intramedullary nail, a targeting guide, a nail cap cannula, and a nail cap; attaching the nail cap cannula to the targeting guide; attaching the targeting guide to the intramedullary nail; attaching the nail cap cannula to the intramedullary nail; detaching the targeting guide from the intramedullary nail and the nail cap cannula; and inserting the nail cap through the nail cap cannula and into engagement with the intramedullary nail.

In still another form thereof, the present disclosure provides a system for use with an intramedullary nail system, the system including a cannula including an inner dimension; an intramedullary nail including a throughbore, the cannula engageable with the intramedullary nail; and a nail cap securable to the intramedullary nail, the nail cap including an outermost width and an overall length, the throughbore of the intramedullary nail configured to prevent passage of at least a portion of the length of the nail cap, and the outermost width of the nail cap is less than the cannula inner dimension.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein:

FIG. 3 is a fragmented perspective view of a portion of the system of FIG. 1, further illustrating a groove on a proximal end of an intramedullary nail;

FIG. 4 is a fragmented perspective view of a portion of the system of FIG. 1, further illustrating features of a targeting guide;

FIG. 5 is a perspective view of a nail cap cannula of the system of FIG. 1;

FIG. 8 is a fragmented perspective view of an intramedullary nail and associated nail cap.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
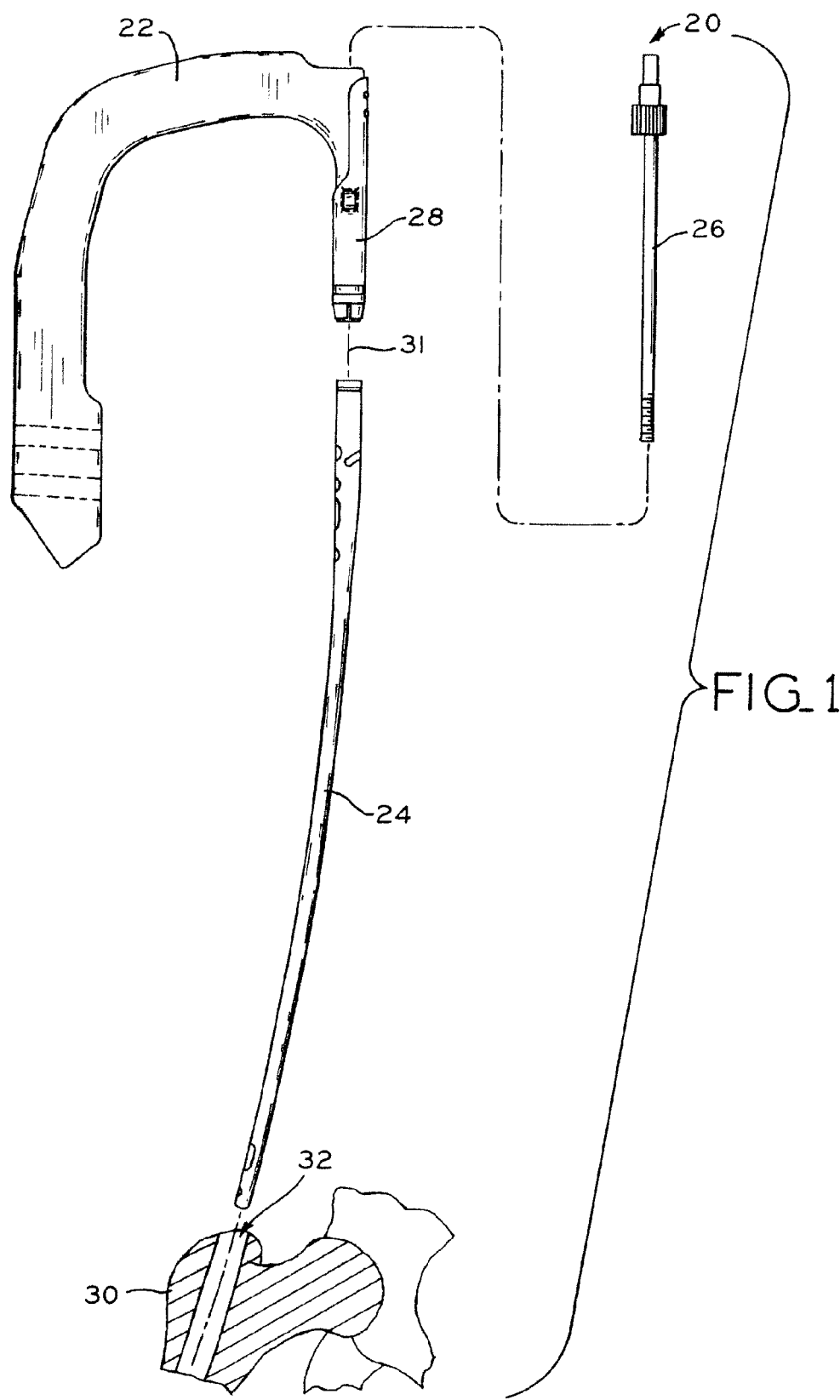
FIG. 1 is an exploded view of an intramedullary nail system according to an exemplary embodiment of the present disclosure.
Figure 2:
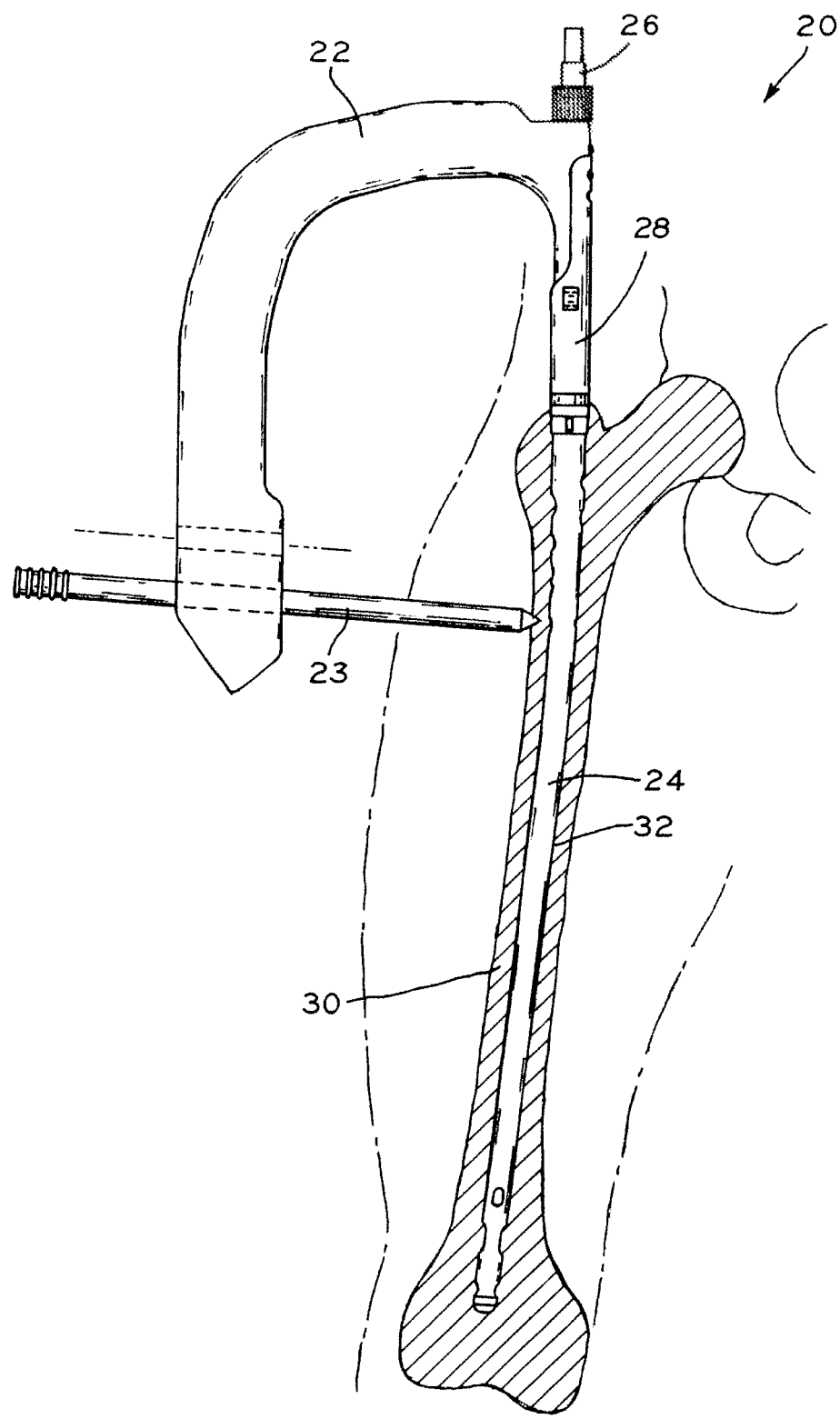
FIG. 2 is an assembled view of the system of FIG. 1, illustrating the nail cap cannula in an engaged position.

Referring to FIGS. 1 and 2, intramedullary (IM) nail system 20 is shown and generally may include targeting guide 22, IM nail 24, tissue protection sleeve 23, connection or locking bolt or screw 26, and nail cap cannula 28. IM nail system 20 is useable in an anatomical structure, such as femur 30, for example, having IM canal 32.

Referring to FIG. 3, targeting guide 22 and IM nail 24 each include features, such as protrusion 34 and protrusion 36, respectively, which, when distal end 38 of targeting guide 22 abuts proximal end 40 of IM nail 24, form junction 42 therebetween to prevent rotation of IM nail 24 relative to targeting guide 22. Throughout this document, the term "distal" is meant to indicate a portion of the instrument farthest away from a user, such as a surgeon, and the term "proximal" is meant to indicate a portion of the instrument closest to the user. IM nail 24 also includes external mating surface or groove 41 proximate proximal end 40. In an exemplary embodiment, groove 41 is located approximately 5 to 10 mm from proximal end 40. In one embodiment, groove 41 has a general hemispherical cross-sectional shape which defines a groove radius. Referring to FIG. 4, targeting guide 22 also includes at least two protrusions or reference features 44, 46 located near proximal end 37 thereof. In an exemplary embodiment, protrusions 44, 46 are generally hemispherically shaped.

Referring now to FIG. 5, nail cap cannula 28 may include proximal end 56 and distal end 58 and may generally include body portion 48 and extension portion 50. In an exemplary embodiment, nail cap cannula 28 may be formed of radiolucent material, such as polyethylene, for example, except for radiopaque element 62, described below. Body portion 48 may generally be hollow as defined by hollow throughbore 54 extending from distal end 58 to extension portion 50. Body portion 48 may include radiopaque element 62, such as a metallic ring inlay, for example. Radiopaque element 62 is located on body portion 48 at a location indicative of the location of proximal end 40 of IM nail 24 when nail cap cannula 28 is in an engaged position with IM nail 24, as described below. Body portion 48 may also include grip portion 64 to facilitate ease of use of nail cap cannula 28 and slots 60 to facilitate outward deformation of distal end 58, as described below. In an exemplary embodiment, grip 64 is oriented transverse to longitudinal axis 31 (FIG. 1) of IM nail 24. Hollow throughbore 54 defines inner circumference or surface 66 on which is located mating surface or protrusion 68 shaped to substantially match the radius and the shape of groove 41 of IM nail 24 (FIG. 3), such as a hemispherical cross-sectional shape. Inner surface 66 defines cannula inner dimension CID of nail cap cannula 28. Throughbore 54 of nail cap cannula 28 is sized and configured to permit passage of nail cap 74 (FIG. 8) therethrough for threaded engagement with IM nail 24, as described below. Extension portion 50 may include contoured portion 52 shaped to substantially match the exterior shape of targeting guide 22. Apertures 70, 72 may be formed in extension portion 50 near proximal end 56 of nail cap cannula 28 and may be configured and sized to accept protrusions 44, 46 on targeting guide 22, as described below.

Figure 6A:
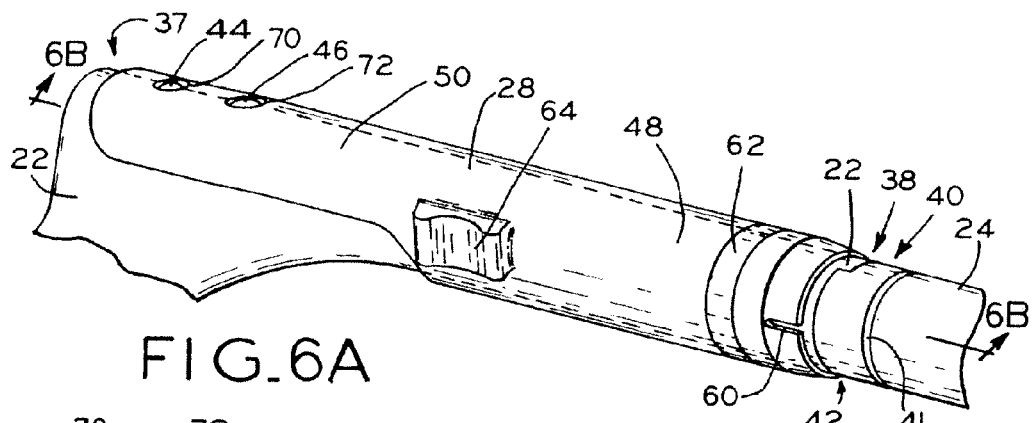
FIG. 6A is a fragmented perspective view of the system of FIG. 1, further illustrating the nail cap cannula in a disengaged position.
Figure 6B:
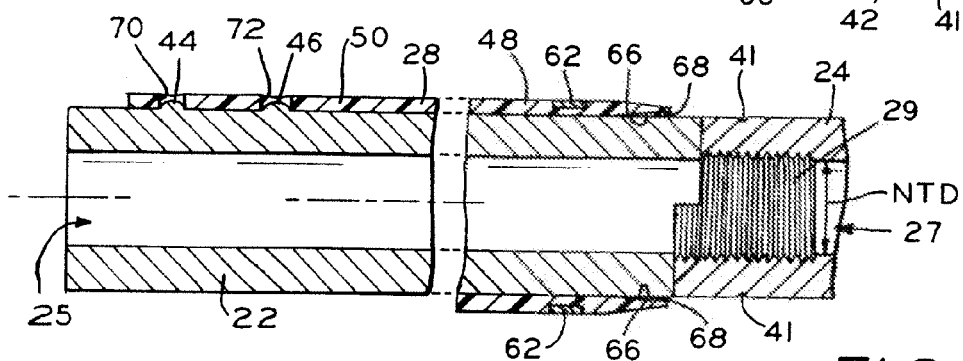
FIG. 6B is a cross-sectional view taken along line 6B-6B of FIG. 6A.
Figure 7A:
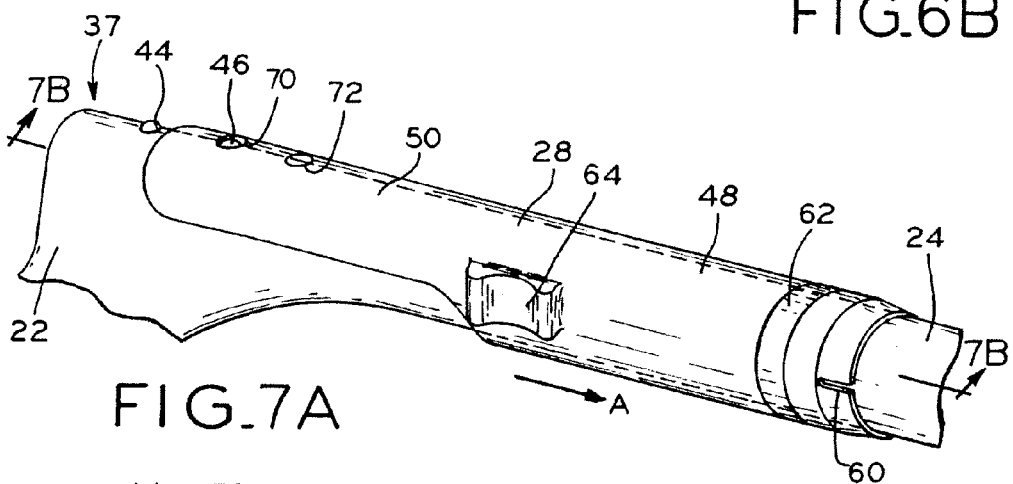
FIG. 7A is a fragmented perspective view of the system of FIG. 1, further illustrating the nail cap cannula in an engaged position.
Figure 7B:
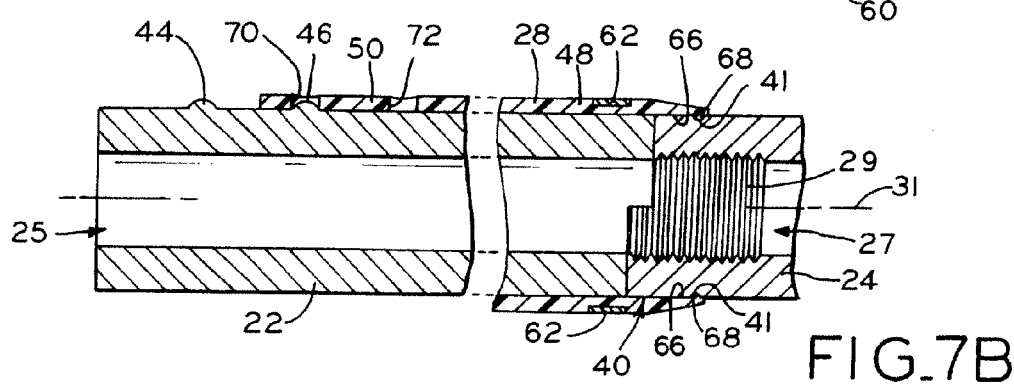
FIG. 7B is a cross-sectional view taken along line 7B-7B of FIG. 7A.

In operation and referring to FIGS. 1, 2, 6A, 6B, 7A, and 7B, nail cap cannula 28 may be used in a method for implanting IM nail 24 in femur 30. As shown in FIGS. 1, 6A, and 6B, distal end 38 of targeting guide 22 is slid through throughbore 54 of nail cap cannula 28 until distal end 38 extends slightly distally of distal end 58 of nail cap cannula 28. Nail cap cannula 28 is then positioned on targeting guide 22 such that protrusions 44, 46 engage apertures 70, 72, respectively, and such that nail cap cannula 28 is not engaged with IM nail 24. In this position, nail cap cannula 28 is in a disengaged position, i.e., disengaged from IM nail 24. IM nail 24 is then positioned on targeting guide 22, i.e., proximal end 40 of IM nail 24 abuts distal end 38 of targeting guide 22 such that protrusions 34, 36 (FIG. 3) engage each other and prevent relative rotational movement between IM nail 24 and targeting guide 22. As shown in FIGS. 7A and 7B, nail cap cannula 28 is then translated toward IM nail 24 by first disengaging apertures 70, 72 and protrusions 44, 46, respectively, and then sliding nail cap cannula 28 in the general direction of Arrow A until protrusion 46 of targeting guide 22 engages aperture 70 of nail cap cannula 28 and protrusion 68 on inner surface 66 of nail cap cannula 28 engages groove 41 on IM nail 24. Slots 60 facilitate deformation of distal end 58 of nail cap cannula 28 when assembled to targeting guide 22 and IM nail 24. In this position, nail cap cannula 28 is in an engaged position, i.e., engaged with IM nail 24. In the engaged position, nail cap cannula 28 maintains a fixed relationship between targeting guide 22 and IM nail 24. Connection bolt 26 is then inserted through throughbore 25 of targeting guide 22 from proximal end 37 and into throughbore 27 of IM nail 24 until a distal end of bolt 26 engages with threads 29 disposed within throughbore 27 of IM nail 24. Connection bolt 26 is tightened into interior threads 29 of IM nail 24. Nail cap cannula 28 maintains targeting guide 22 and IM nail 24 in an engaged position while connection bolt 26 is tightened.

Nail cap cannula 28 is then returned to the disengaged position, as shown in FIGS. 1, 6A, and 6B, after which IM nail 24 is impacted into femur 30 via a suitable impaction device (not shown). Nail cap cannula 28 is then moved again to the engaged position, as shown in FIGS. 2, 7A, and 7B. A surgeon may visually confirm the location of proximal end 40 of IM nail 24 by viewing radiopaque element 62 in an X-ray or other image of femur 30 and IM nail 24. As shown in FIG. 7B, when nail cap cannula 28 is in the engaged position, radiopaque element 62 is substantially aligned with proximal end 40 of IM nail 24. Because nail cap cannula 28 is formed primarily of a radiolucent material, nail cap cannula 28 does not obstruct the view of the surgeon when visually confirming the location of proximal end 40 of IM nail 24. Moreover, radiopaque element 62 may have a larger diameter than IM nail 24 and targeting guide 22 such that radiopaque element 62 is further distinguished from IM nail 24 and targeting guide 22 in the image of femur 30. Once the location of proximal end 40 of IM nail 24 is confirmed, connection bolt 26 is disengaged from IM nail 24 and removed from targeting guide 22. Targeting guide 22 is then disengaged from IM nail 24 and nail cap cannula 28 by manipulating targeting guide 22 to disengage protrusions 44, 46 with either or both apertures 70, 72, after which targeting guide 22 may be slid out of engagement with nail cap cannula 28 and removed from proximity to femur 30.

Once targeting guide 22 and connection bolt 26 are removed, nail cap cannula 28 remains attached to IM nail 24 via interaction of groove 41 of IM nail 24 and protrusion 68 on inner surface 66 of nail cap cannula 28. Nail cap 74 (FIG. 8) is then inserted through body portion 48 of nail cap cannula 28 and external threads 76 of nail cap 74 (FIG. 8) engage with interior threads 29 of throughbore 27 in IM nail 24. Nail cap 74 defines overall length OL and outermost nail cap width NW, and throughbore 27 of IM nail 24 defines nail throughbore dimension NTD. In an exemplary embodiment, outermost nail cap width NW defines a dimension greater than nail throughbore dimension NTD and less than cannula inner dimension CID. Throughbore 27 of IM nail 24 prevents passage of at least a portion of the overall length OL of nail cap 74, such as head 75 of nail cap 74. Nail cap cannula 28 extends through the soft tissue of a patient to femur 30, thereby providing an unobstructed passageway or portal for passage of nail cap 74 therethrough. Nail cap cannula 28 prevents tissue and other bodily fluids from interfering with nail cap 74 during insertion thereof. Furthermore, nail cap cannula 28 facilitates maintaining a proper trajectory of nail cap 74 during movement towards IM nail 24 such that accurate alignment of threads 76 of nail cap 74 and threads 29 of IM nail 24 may be achieved. Moreover, nail cap cannula 28 ensures an unobstructed trajectory of a surgical instrument or tool used to insert and engage nail cap 74 with IM nail 24.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:
1. A nail cap cannula system comprising:
an intramedullary nail having an external surface including an external mating feature adjacent to a first end of the nail;
a nail cap cannula having a substantially hollow body portion including a first end and a second end with a bore extending therebetween, the bore having an inner dimension sized to receive at least a portion of the intramedullary nail, the first end including an internal surface having an internal mating feature configured to mate with the external mating feature of the intramedullary nail; and a targeting guide having a proximal handle portion and a distal end, the distal end having an outer dimension that is smaller than the inner dimension of said bore of said nail cap cannula, wherein the distal end of the targeting guide is receivable within the hollow body portion of said nail cap cannula;

wherein, when the intramedullary nail, the nail cap cannula and the targeting guide are assembled, the nail cap cannula moves between a disengaged position relative to the intramedullary nail, in which the internal mating feature of the nail cap cannula is disengaged from the external mating feature of the intramedullary nail, and an engaged position relative to the intramedullary nail, in which the internal mating feature of the nail cap cannula is engaged with the external mating feature of the intramedullary nail.

2. The system of claim 1, wherein the internal mating feature of the nail cap cannula comprises a protrusion extending from the internal surface into the bore and the external mating feature of the intramedullary nail comprises a groove formed in the external surface, said protrusion engageable with said groove to maintain a fixed relationship between said targeting guide and the intramedullary nail.

3. The system of claim 1, the nail cap cannula further comprising an extension portion connected to the body portion at the second end, the extension portion including at least two apertures, the targeting guide further comprising a first protrusion and a second protrusion, and wherein when the nail cap cannula is in the disengaged position the at least two apertures engage the first protrusion and the second protrusion of the targeting guide, and when the nail cap cannula is in the engaged position only one of the at least two apertures engages one of the first protrusion or the second protrusion of the targeting guide.

4. The system of claim 3, wherein the extension portion comprises a contoured shape substantially matching a shape of the targeting guide.

5. The system of claim 1, wherein the body portion includes a radiopaque portion, the radiopaque portion substantially aligned with a proximal end of the intramedullary nail when the nail cap cannula is in the engaged position.

6. The system of claim 5, wherein the radiopaque portion comprises a metallic ring inlay.

7. The system of claim 1, wherein the body portion includes a grip portion, the grip portion oriented transverse to a longitudinal axis of the intramedullary nail.

8. The system of claim 1, wherein the body portion includes at least one slot proximate the first end.

9. The system of claim 1, wherein the distal end of the targeting guide is configured to mate with the first end of the intramedullary nail.

10. The system of claim 9, wherein the distal end of the targeting guide and the fist end of the intramedullary nail are configured to mate to maintain a fixed relationship and to prevent rotation between said targeting guide and the intramedullary nail.

11. The system of claim 1, wherein the external surface of the intramedullary nail defines a nail outer dimension that is substantially equal to the outer dimension of the targeting guide, whereby the inner dimension of the nail cap cannula is sized to receive both the distal end of the targeting guide and the external surface of the intramedullary nail.

12. A method of performing a surgical procedure on an anatomical structure using an intramedullary nail system including a targeting guide, a nail cap, and an intramedullary nail, the method comprising the steps of:

providing an intramedullary nail, a targeting guide, a nail cap cannula, and a nail cap;

attaching the nail cap cannula to the targeting guide;

attaching the targeting guide to the intramedullary nail;

attaching the nail cap cannula to the intramedullary nail;

detaching the targeting guide from the intramedullary nail and the nail cap cannula;

after said step of detaching the targeting guide, inserting the nail cap through the nail cap cannula and into engagement with the intramedullary nail; and removing the nail cap cannula from the intramedullary nail.

13. The method of claim 12, further comprising the step, subsequent to the steps of attaching the nail cap cannula to the targeting guide and attaching the targeting guide to the intramedullary nail, of inserting the intramedullary nail into the anatomical structure.

14. The method of claim 12, wherein the step of attaching the nail cap cannula to the targeting guide precedes the step of attaching the targeting guide to the intramedullary nail.

15. The method of claim 14, wherein the steps of attaching the nail cap cannula to the targeting guide, attaching the targeting guide to the intramedullary nail, and attaching the nail cap cannula to the intramedullary nail precede the step of detaching the targeting guide from the intramedullary nail and the nail cap cannula.

16. The method of claim 15, wherein the steps of attaching the nail cap cannula to the targeting guide, attaching the targeting guide to the intramedullary nail, attaching the nail cap cannula to the intramedullary nail, and detaching the targeting guide from the intramedullary nail and the nail cap cannula precede the step of inserting the nail cap through the nail cap cannula.

17. The method of claim 12, wherein the nail cap cannula remains attached to the intramedullary nail after detaching the targeting guide from the intramedullary nail and the nail cap cannula.

18. The method of claim 12, further comprising the steps of providing a radiopaque portion in the nail cap cannula and identifying a proximal end of the intramedullary nail using the radiopaque portion of the nail cap cannula.

* * * * *